United States Patent [19]
Yewey et al.

[11] Patent Number: 5,744,153
[45] Date of Patent: Apr. 28, 1998

[54] LIQUID DELIVERY COMPOSITIONS

[75] Inventors: Gerald L. Yewey; Nancy L. Krinick; Richard L. Dunn, all of Fort Collins, Colo.; Michael L. Radomsky, Mountain View; Gerbrand Brouwer, Menlo Park, both of Calif.; Arthur J. Tipton, Birmingham, Ala.

[73] Assignee: Atrix Laboratories, Inc., Fort Collins, Colo.

[21] Appl. No.: 871,492

[22] Filed: Jun. 9, 1997

Related U.S. Application Data

[60] Continuation of Ser. No. 487,979, Jun. 7, 1995, abandoned, which is a division of Ser. No. 225,140, Apr. 8, 1994, abandoned.

[51] Int. Cl.[6] .................... A61F 2/00; A61K 9/127; A61K 9/52
[52] U.S. Cl. .................... 424/426; 424/422; 424/423; 424/450; 424/459; 525/937; 514/900; 604/890.1; 604/891.1; 604/27; 604/48; 604/49; 604/54
[58] Field of Search .................... 424/422, 423, 424/426, 450, 489; 525/937; 514/900, 58; 604/890.1, 891.1, 27, 48, 49, 54

[56] References Cited

U.S. PATENT DOCUMENTS

| | | | |
|---|---|---|---|
| 2,155,658 | 4/1939 | Herrmann | 167/58 |
| 3,887,699 | 6/1975 | Yolles | 424/19 |
| 4,265,247 | 5/1981 | Lenz et al. | 128/335.5 |
| 4,408,023 | 10/1983 | Gould et al. | 525/454 |
| 4,450,150 | 5/1984 | Sidman | 424/1.1 |

(List continued on next page.)

FOREIGN PATENT DOCUMENTS

| | | |
|---|---|---|
| 0537559 | 4/1993 | European Pat. Off. . |
| 0539751 | 5/1993 | European Pat. Off. . |
| 0560014 | 9/1993 | European Pat. Off. . |
| 0586838 | 3/1994 | European Pat. Off. . |
| 0649662 | 4/1995 | European Pat. Off. . |
| 2017113 | 10/1979 | United Kingdom . |
| WO 85/02092 | 5/1985 | WIPO . |

OTHER PUBLICATIONS

Gref et al., *Science,* 263, 1600–1602 (1994).
Juni et al., *Chem. Pharm Bull.,* 33, 1609–1614 (1985).
Ouchi et al., *J. Controlled Release,* 12, 143–153 (1990).
Wakiyama, *Chem. Pharm Bull.,* 29, 3363–68 (1981).
Encyclopedia of Polymer Science and Engineering, vol. 2, pp. 236–237 (Biodegradable Polymers), John Wiley & Sons, Inc. (1985).
Billmeyer, Textbook of Polymer Science (Third Edition), pp. 390–391, John Wiley & Son, New York.
Gilding, Biodegradable Polymers (Chapter 9), pp. 210–232, Biocompatibility of Clinical Implant Materials.
Hawley's Condensed Chemical Dictionary (11th Ed.) pp. 224, 555 and 567, Van Nostrand Reinhold Co., NY, NY.
Holland, Polymers for Biodegradable Medical Devices, 1. The Potential of Polyesters and Controlled Macromolecular Release Systems, J. of Controlled Release 4: 155–180 (1986).

*Primary Examiner*—Gollamudi S. Kishore
*Attorney, Agent, or Firm*—Merchant, Gould, Smith, Edell, Welter & Schmidt

[57] ABSTRACT

Improved biocompatible liquid delivery compositions, which are useful for the formation of sustained release delivery systems for active agents, are provided. The compositions include liquid formulations of a biocompatible polymer or prepolymer in combination with a controlled release component. The controlled release component includes an active agent. These compositions may be introduced into the body of a subject in liquid form which then solidify or cure in situ to form a controlled release implant or a film dressing. The liquid delivery compositions may also be employed ex situ to produce a controlled release implant. Methods of forming a controlled release implant and employing the liquid formulations in the treatment of a subject are also provided.

9 Claims, 3 Drawing Sheets

RELEASE OF CHLORIN e6
POLYMER BOUND DRUG vs. FREE DRUG
0.5% DRUG IN 75/25 PLG/DMSO

U.S. PATENT DOCUMENTS

| | | | |
|---|---|---|---|
| 4,451,452 | 5/1984 | Deibig et al. | 424/78 |
| 4,622,219 | 11/1986 | Haynes | 424/38 |
| 4,631,188 | 12/1986 | Stoy et al. | 424/81 |
| 4,685,883 | 8/1987 | Jernberg | 433/215 |
| 4,721,613 | 1/1988 | Urquhart | 424/19 |
| 4,745,160 | 5/1988 | Churchill et al. | 525/415 |
| 4,780,320 | 10/1988 | Baker | 424/493 |
| 4,818,542 | 4/1989 | DeLuca et al. | 424/491 |
| 4,861,627 | 8/1989 | Mathiowitz et al. | 427/213.31 |
| 4,897,268 | 1/1990 | Tice et al. | 424/422 |
| 4,912,141 | 3/1990 | Kronman | 521/61 |
| 4,919,939 | 4/1990 | Baker | 424/493 |
| 4,933,182 | 6/1990 | Higashi et al. | 424/435 |
| 4,938,763 | 7/1990 | Dunn et al. | 604/891.1 |
| 4,962,091 | 10/1990 | Eppstein et al. | 514/2 |
| 4,981,696 | 1/1991 | Loomis | 424/486 |
| 5,013,553 | 5/1991 | Southard | 424/426 |
| 5,019,400 | 5/1991 | Gombotz et al. | 424/497 |
| 5,049,386 | 9/1991 | Eppstein et al. | 424/427 |
| 5,077,049 | 12/1991 | Dunn et al. | 424/426 |
| 5,149,543 | 9/1992 | Cohen et al. | 424/499 |
| 5,176,907 | 1/1993 | Leong | 424/78.08 |
| 5,188,837 | 2/1993 | Domb | 424/450 |
| 5,192,741 | 3/1993 | Orsolini et al. | 514/4 |
| 5,227,157 | 7/1993 | McGinity et al. | 424/78.02 |
| 5,238,714 | 8/1993 | Wallace et al. | 427/213.36 |
| 5,271,961 | 12/1993 | Mathiowitz et al. | 427/213.31 |
| 5,278,201 | 1/1994 | Dunn et al. | 523/113 |
| 5,278,202 | 1/1994 | Dunn et al. | 523/113 |
| 5,324,519 | 6/1994 | Dunn et al. | 424/426 |
| 5,324,520 | 6/1994 | Dunn et al. | 424/435 |
| 5,326,568 | 7/1994 | Giampapa | 424/426 |
| 5,340,849 | 8/1994 | Dunn et al. | 523/113 |
| 5,368,858 | 11/1994 | Hunziker | 424/423 |
| 5,368,859 | 11/1994 | Dunn et al. | 424/426 |

LIQUID DELIVERY COMPOSITIONS

This is a Continuation of application Ser. No. 08/487,979, filed Jun. 7, 1995 now abandoned, which is a divisional of Ser. No. 08/225,140, filed Apr. 8, 1994, now abandoned, which application is incorporated herein by reference.

BACKGROUND OF THE INVENTION

A variety of approaches have been developed to permit the continuous, sustained release of drugs into a subject. These controlled release systems are designed to protect the drug from the environment prior to delivery while permitting the controlled release of the drug to a targeted area. All of the currently available approaches, however, suffer from one or more disadvantages or limitations.

A number of conventional controlled release systems are based on microstructures, such as lipospheres, liposomes, microcapsules, microparticles, and nanoparticles. The microstructures are typically introduced into the body of a subject in the form of a dispersion. While microstructure dispersions are useful for many applications, these systems cannot be used to form a continuous barrier film or a solid implant with the structural integrity required for prosthetic applications. In addition, when inserted into a body cavity where there is considerable fluid flow, e.g., the mouth or eye, microstructures may be poorly retained due to their small size and discontinuous nature. Another limitation of such microstructure-based systems is the lack of reversibility of introduction without extensive and complex surgical intervention. If complications arise after their introduction, systems based on microstructures are considerably more difficult to remove from the body of a subject than a solid implant.

Conventional controlled delivery systems may also be prepared as macrostructures. An active agent, such as a drug, may be blended with a polymer. The blend is then shaped into a specific form such as a cylinder, disc or fiber for implantation. Alternatively, a solid porous implant, which is formed from a biodegradable polymer, may serve as a container to hold one of the controlled release microsystems described above in place in a subject. With either of these solid implant approaches, the drug delivery system is typically inserted into the body through an incision. These incisions are often larger than desired and can lead to a reluctance on the part of the subject to accept such a treatment.

Both microstructures and macrostructures of conventional controlled release systems may be prepared from polymer-drug conjugates. As such they have the same disadvantages as those described earlier for similar structures of other conventional controlled release systems. In addition, polymer-drug conjugates may be prepared from water-soluble polymers so that they cannot be retrieved if needed. Because polymer-drug conjugates afford a variety of drug release mechanisms, such as hydrolysis, enzymatic cleavage, or photocleavage and permit a greater degree of control over release rates, it would be desirable if they could be prepared without the above disadvantages.

The disadvantages of the systems described above have been overcome to some extent by the development of drug delivery systems which can be administered as a liquid (e.g., via syringe) and are subsequently transformed in situ into a solid implant. For example, liquid polymeric compositions for use as biodegradable controlled release delivery systems are described in U.S. Pat. Nos. 4,938,763, 5,278,201 and 5,278,202. These compositions may be administered to the body in a liquid state. Once in the body, the composition coagulates or cures to form a solid. One such polymeric composition includes a nonreactive thermoplastic polymer or copolymer dissolved in a water-soluble solvent. This polymeric solution is introduced into the body, e.g., via syringe, where it "sets up" or solidifies upon dissipation or diffusion of the solvent into surrounding body fluids. The other injectable polymeric composition is based on a thermoset system of prepolymers that can be cured in situ. This polymeric system includes reactive liquid oligomeric prepolymers which cure by cross linking to form solids, usually with the aid of a curing agent.

These injectable liquid polymeric systems have a number of distinct advantages. While avoiding the requirement for an incision, the liquid delivery systems permit the formation of an implant with sufficient structural integrity to be used as prosthetic devices or as a continuous barrier film. Because a solid implant is formed, these liquid systems also avoid the problems of dissipation observed with microstructure dispersions in those portions of the body which experience considerable fluid flow. Despite these advantages, the liquid delivery systems currently available for forming implants in situ lack certain desirable characteristics.

When a liquid delivery system including a biodegradable polymer and an active agent dissolved in a water-soluble solvent, comes into contact with an aqueous medium such as a body fluid, the solvent dissipates or diffuses into the aqueous medium. As the polymer precipitates or coagulates to form a solid matrix, the active agent is trapped or encapsulated throughout the polymeric matrix. The release of the active agent then follows the general rules for the dissolution or diffusion of a drug from within a polymeric matrix. The formation of the solid matrix from the liquid delivery system is, however, not instantaneous but typically occurs over a period of several hours. During this initial period, the rate of diffusion of the active agent may be much more rapid than the rate of release that occurs from the subsequently formed solid matrix. This initial burst affect (i.e. the amount of active agent released in the first 24 hours) may result in the loss or release of a large amount of the active agent prior to the formation of the solid matrix. If the active agent is particularly toxic, this initial release or burst is likely to lead to toxic side effects and may cause damage to the adjacent tissues.

The development of liquid delivery systems that would allow the in situ formation of an implant while reducing or eliminating the initial burst effect would represent a significant advancement. Such delivery systems would permit higher concentrations of an active agent to be safely incorporated into an implant. The efficiency of such systems would also be improved, since a much greater percentage of the active agent would remain in the implant for sustained release and not be lost during the initial burst. Optimally, the liquid delivery system would afford a number of modes of controlling the release of an active agent from the system. These advantages would extend the application of such treatments as well as reducing the possibility of toxic side effects. There is, therefore, a continuing need for controlled release systems which can be introduced in liquid form to form a solid implant in situ and which will facilitate the sustained release of an active agent in a subject's body without creating an initial burst of active agent.

SUMMARY OF THE INVENTION

The present invention provides liquid compositions which are useful for the delivery of active agents in vivo and permit the initial burst of active agent to be controlled more effectively than previously possible. This can be done, for example, by incorporating the active agent into a controlled release component and combining the controlled release component with the liquid polymer systems described in U.S. Pat. Nos. 4,938,763, 5,278,201 and 5,278,202. The controlled release component may include a microstructure (e.g. a microcapsule) or macrostructure (e.g. a film or fiber) controlled release system, a molecular controlled release system (e.g. a polymer/drug conjugate) or combinations thereof. The resulting liquid delivery compositions may include either liquid or solution formulations of a biocompatible prepolymer, polymer or copolymer in combination with the controlled release component. These liquid delivery compositions may be introduced into the body of a subject in liquid form. The liquid composition then solidifies or cures in situ to form a controlled release implant.

The formulation employed to form the controlled release implant in situ may be a liquid delivery composition which includes a biocompatible polymer which is substantially insoluble in aqueous medium, an organic solvent which is miscible or dispersible in aqueous medium, and the controlled release component. The biocompatible polymer is substantially dissolved in the organic solvent. The controlled release component may be either dissolved, dispersed or entrained in the polymer/solvent solution. In a preferred embodiment, the biocompatible polymer is biodegradable and/or bioerodable.

The liquid delivery composition may be used to form a solid controlled release implant on either the inside or outside of the subject's body. In one embodiment of the invention, the liquid delivery composition is introduced to an implant site in the subject where the composition solidifies to form the controlled release implant upon contact with a body fluid. In another embodiment of the invention, a solid implant may be formed outside the subject by contacting the liquid composition with an aqueous medium. The solid implant may then be inserted into an implant site in the subject.

In yet another embodiment of the present invention, the liquid delivery composition may be used to form a film dressing on a tissue of a subject. An amount (effective to form a film dressing) of the liquid composition is dispensed onto the tissue, such as by spraying, painting or squirting, and the film dressing is formed on the tissue by contacting the liquid delivery composition with an aqueous medium.

The invention also includes a method for treating a subject with an active agent by administering the liquid delivery composition to an implant site in a subject to form a solid controlled release implant in situ. The treatment of a subject with the active agent may also be carried out by inserting into the subject a solid sustained release implant formed outside the subject by contacting the liquid delivery composition with an aqueous medium. The present invention also encompasses a method which includes treating a subject's tissue (e.g. injured tissue) by administering an effective amount of the liquid delivery composition to form a film dressing on the tissue.

In another embodiment of the invention, the controlled release component incorporating the active agent may also be introduced into a subject's body as part of a liquid delivery composition which includes a liquid, biocompatible prepolymer. The liquid prepolymer has at least one polymerizable ethylenically unsaturated group (e.g., an acrylic-ester-terminated prepolymer). If a curing agent is employed, the curing agent is typically added to the composition just prior to use. The prepolymer remains a liquid for a short period after the introduction of the curing agent. During this period the liquid delivery composition may be introduced into a body, e.g., via syringe. The mixture then solidifies in situ to form a solid implant. Other embodiments of the liquid delivery system may also include a pore-forming agent or an organic solvent which is miscible or dispersible in aqueous medium in addition to the prepolymer and controlled release component. Alternatively, the pore-forming agent or the organic solvent may be added to the liquid prepolymer composition together with or just after the addition of the curing agent. When a liquid delivery composition including the pore-forming agent or the organic solvent in combination with the prepolymer is employed, the implant which is formed includes a solid microporous polymer matrix having the controlled release component embedded therewithin.

Another embodiment of the present invention is directed to a method of treating a subject with the active agent which includes introducing the liquid prepolymer composition into the subject. Yet another embodiment of the invention provides for treating an injured tissue of a subject including administering on the injured tissue an effective amount of the liquid prepolymer composition to form a film dressing.

Another method to provide liquid compositions which are useful for the delivery of active agents in vivo and permit the initial burst of active agent to be controlled more effectively than previously possible is to conjugate the active agent with a water-insoluble biocompatible polymer and dissolve the resultant polymer-active agent conjugate in a biocompatible solvent to form a liquid polymer system similar to that described in U.S. Pat. Nos. 4,938,763, 5,278,201 and 5,278,202. The water-insoluble biocompatible polymers may be those described in the above patents or related copolymers. In addition, the liquid polymer system may also include a water-insoluble biocompatible polymer which is not conjugated to the active agent. In one embodiment of the invention, these liquid compositions may be introduced into the body of a subject in liquid form. The liquid composition then solidifies or coagulates in situ to form a controlled release implant where the active agent is conjugated to the solid matrix polymer. In another embodiment of the invention, a solid implant may be formed outside the subject by contacting the liquid composition with an aqueous medium. The solid implant may then be inserted into an implant site in the subject. In yet, another embodiment of the present invention, the liquid delivery composition may be used to form a film dressing on a tissue of a subject.

Figure 1:
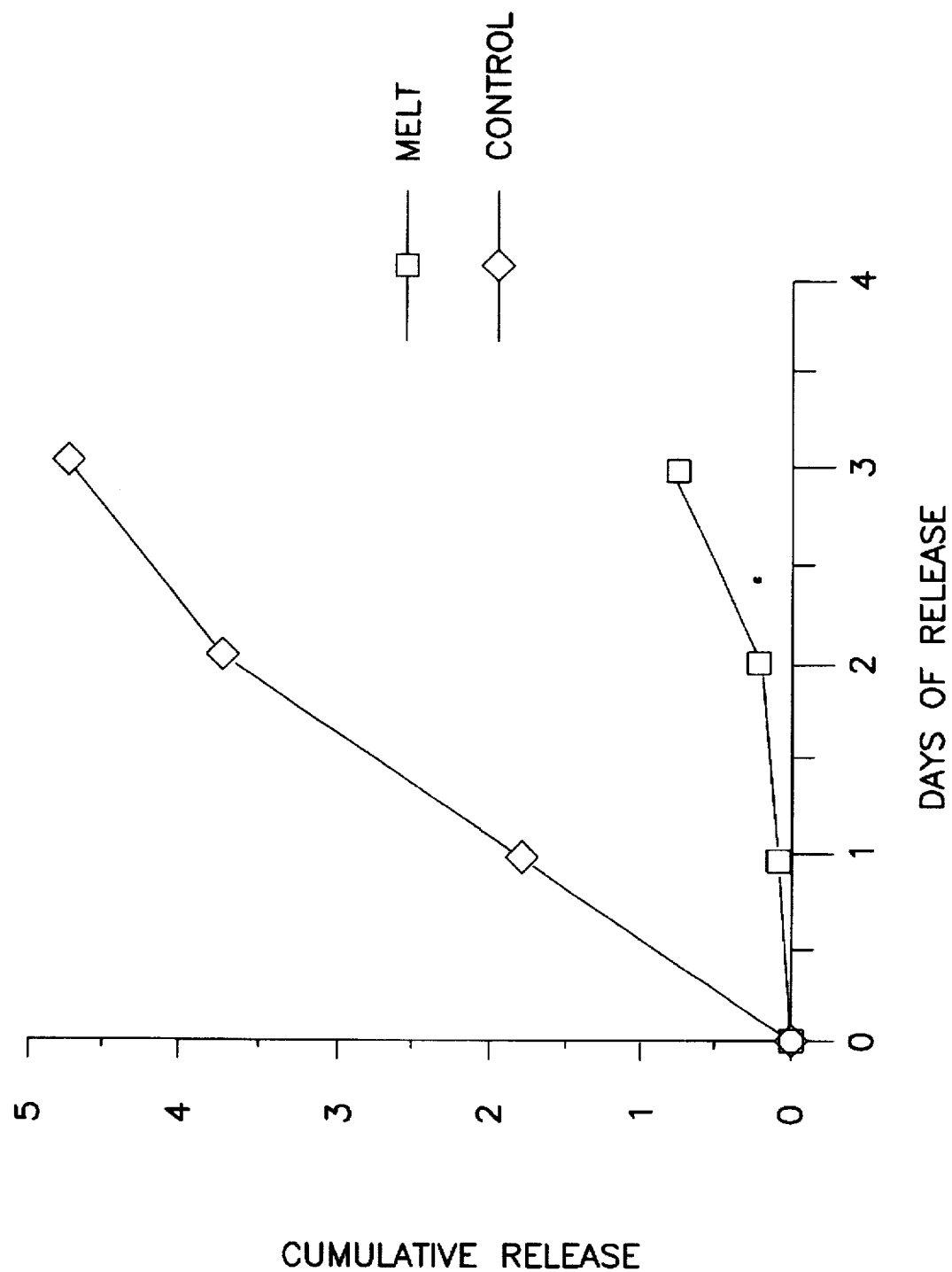
FIG. 1 shows the cumulative amount of naltrexone released from formulations in 75/25 poly(D,L-lactide-co-glycolide) (PLG) dissolved in NMP. The formulations included either free naltrexone or microparticles prepared by melt fusion of naltrexone and poly(D,L-lactide) (PLA). Each of the formulations contained 5.0% w/w naltrexone (on a free drug basis).

methacrylamide)/N-methacryloylglycine copolymer. Each of the formulations contained 0.5% w/w chlorin $e_6$ (on a free drug basis).

DETAILED DESCRIPTION OF THE INVENTION

The present invention provides biocompatible liquid delivery compositions which may be used to form solid structures which permit an active agent to be delivered in a sustained, controlled manner. The compositions are typically administered in liquid form. After insertion, the compositions solidify or cure ("set up") to form a solid or gelatinous matrix ("implant"), which is substantially insoluble in aqueous media, such as body fluids. Based on the relative partitioning properties of the active agent in a given formulation, an initial release of a comparatively large amount of the active agent may be observed. In some instances this initial release may not be problematic, e.g., the active agent may be a drug with a large therapeutic window. In other cases, however, the initial release may cause damage to adjacent tissues or lead to toxic side effects.

Liquid Polymer System with Controlled Release Component

The initial burst may be decreased or avoided by modifying the physical state of the active agent, e.g., incorporating the active agent into a controlled release component which is then dissolved, dispersed or entrained in the liquid delivery composition. For example, the controlled release component may include microstructures, macrostructures, conjugates, complexes or low water-solubility salts. In principle, the additional time required to release the active agent from the controlled release component will enable the formulation to solidify into a solid implant without the initial loss of a substantial amount of the active agent. Thus, the present compositions are useful for the delivery of active agents in vivo and permit the initial burst of active agent to be controlled more effectively than previously possible.

Examples of suitable controlled release components include microstructures such as microparticles, nanoparticles, cyclodextrins, microcapsules, micelles and liposomes. The controlled release component may also include macrostructures such as fibers, rods, films, discs or cylinders. Suitable controlled release components also include low water-solubility salts of the active agent and complexes or conjugates in which the active agent is operatively associated with a carrier molecule. Further included within the definition of the controlled release component are combinations of the above approaches. For example, the controlled release component may be a microstructure, such as a microcapsule, which includes the active agent as part of a complex, conjugate, or low water-solubility salt.

If the liquid delivery composition is to be introduced into the subject by injection, the size of the microcapsules or microparticles is typically limited to no more than 500 microns, and preferably no more than 150 microns. Microstructures larger than 500 microns are difficult to deliver via syringe or rubber tube and may be uncomfortable or irritating to the surrounding tissues. In other applications, the controlled release component may, however, include a macrostructure such as a fiber, a film or a larger polymer bead. These may be dispersed, entrained or associated with the liquid portion of the liquid delivery composition such that the composition solidifies to form a matrix with the macrostructure embedded therein. Alternatively, the liquid portion may act as an adhesive to hold the macrostructure in place at an implant site in the subject's body. The macrostructures are larger than 500 microns. The upper limits on size of the macrostructures will depend on the particular application.

Once formed into a solid matrix, the resulting implant provides at least dual modes for controlling the release of the active agent—a first mode based on the rate of release of the active agent from the controlled release component and a second mode based on the release from the implant matrix. The second mode is governed by the rate of biodegradation and/or bioerosion of the implant material and may also be governed by diffusion where the implant is a microporous matrix. The rate of release from the controlled release component may also be governed by the rate of biodegradation and/or bioerosion of a polymer matrix, e.g., where the controlled release component is a polymeric microparticle or microcapsule. The release rate may also depend on a variety of other processes, such as where the controlled release component includes a conjugate of a carrier molecule and the active agent. The rate of release of the active agent from the conjugate may also be governed by the rate of breakdown of the conjugate.

The choice of a particular controlled release component will depend on the physical characteristics of the active agent (e.g., solubility, stability, etc.) and the desired properties of the liquid composition and the resulting implant. The controlled release component may include one or more of a variety of materials. The controlled release component may include a polymer, e.g., as the matrix of a microparticle, as the coating of a microcapsule, or as the carrier molecule of an active agent conjugate. The controlled release component may also include a hydrophobic counterion, such as when the active agent is present as a low water solubility salt. The controlled release component may include combinations of the above, such as where the controlled release component includes as active agent-conjugate encapsulated within a polymer coating.

The controlled release component may include a plurality of microstructures such as microparticles, microcapsules or nanoparticles. The microparticles or microcapsules are typically between 1 and 500 microns in size, although smaller particles may be used (e.g., nanoparticles which range in size from 10 nanometers to 1000 nanometers). Microcapsules in this context are defined as reservoir systems in which a simple reservoir of material which includes the active agent is surrounded by a membrane shell. The reservoir may contain only the active agent or it may include other materials such as a polymer matrix or a release rate modification agent. Alternatively, the reservoir may include the active agent incorporated as part of a conjugate, a complex or a low water solubility salt. Microparticles are small monolithic entities in which the active agent is distributed throughout the particle matrix, typically in a random fashion. However, many practical formulations fall between these two definitions. For example, microcapsules may agglomerate during the microencapsulation process. In other instances, the size of the active agent particles contained in a "microcapsule" system may be of the same order as the size of the microcapsules themselves. For the purposes of this invention the term "microstructure" is defined to include microparticles, nanoparticles, microcapsules or any related intermediate forms. Various physical and chemical methods for preparing these microstructures have been developed and the technology is well established and well documented. See for example Patrick V. Deasy, "Microencapsulation and Related Drug Processes," Marcel Dekker Inc., New York (1984). A variety of exemplary methods of preparing microcapsules and microparticles are known (see e.g., U.S. Pat. Nos. 4,061,254, 4,818,542, 5,019,400 and 5,271,961; and Wakiyama et al., *Chem. Pharm Bull.*, 29, 3363–68 (1981)). Depending on the chemical and physical properties desired, a number of these methods may be used to prepare microcapsules or microparticles.

The microparticles may be in the form of lipospheres. In this instance, the microparticles include a phospholipid and optionally, an inert solid material, such as a wax. Lipospheres are solid, water-insoluble microparticles which have a layer of the phospholipid embedded on their surface. The core of the lipospheres contain either a solid active agent or an active agent that is dispersed in the inert solid material (see, e.g., U.S. Pat. No. 5,188,837).

Liposomes containing the active agent typically are formed in an aqueous solution by one of a well-known methods (see e.g. U.S. Pat. No. 5,049,386). The aqueous solution containing the liposomes may be incorporated in the compositions of the present invention, for example by forming a water-in-oil emulsion of this solution in a liquid pre-polymer. After curing, a polymer matrix with the liposomes embedded therein is formed.

Nanoparticles are carriers for drugs or other active molecules which are prepared in the nanometer size range (10 nm–1000 nm). Drugs can be incorporated into nanoparticles using colloidal coacervation of polymers, absorption on the surface of solid colloidal polymeric carriers, coating of the particles by polymerization, polycondensation, or coacervation, solidifying spherical micelles under nanocompartmentation by polymerization or polycondensation, and interfacial polymerization techniques using electrocapillary emulsification.

For example, the nanoparticles may include nanospheres as described in Gref et al., *Science*, 263, 1600–1602 (1994). The nanospheres may be formed from diblock polymers which have a lipophilic block and a hydrophilic block. The active agent is distributed throughout the nanosphere and is typically present as a molecular dispersion throughout the lipophilic core of the nanospheres. When present in the nanospheres at a high loading, however, a phase separation of the active agent may occur leading to the formation of aglomerates or crystals of active agent.

The liquid delivery compositions may also include a number of macrostructures such as fibers, rods, films, discs or cylinders. These macrostructures may consist of reservoir systems in which the active agent is surrounded by a membrane which controls the rate of release, or monolithic systems in which the active agent is distributed throughout the macrostructure matrix.

The present liquid delivery compositions, offer the advantage of safe, sustained release of a active agent without an initial burst effect. In another embodiment of the invention, this may be achieved by incorporating the active agent (e.g., a drug) in a controlled release component which includes a conjugate. Conjugates in this context are defined as a controlled release component in which the active agent is covalently bonded to a carrier molecule. By covalently bonding the active agent to the carrier molecule, the solubility and transport properties of the active agent are altered. Preferably, the carrier molecule has no biological activity of its own and is readily biodegraded. The carrier molecule is typically a polymer but may also be a smaller organic molecule. For instance, the active agent may be covalently bonded to a small molecule such as stearic acid though an ester or amide linkage, thereby decreasing the water solubility of the active agent.

The polymers used to prepare drug conjugates may be water-soluble, e.g. polyethylene glycol, poly-L-aspartic acid, poly(glutamic acid), polylysine, poly(malic acid), dextran, and copolymers of N-(2-hydroxypropyl) methacrylamide (HPMA). The polymers employed to prepare drug conjugates may also include water-insoluble polymers such as polyglycolide, poly(DL-lactide) (PLA), polycaprolactone (PCL), polyorthoesters, polycarbonates, polyamides, polyanhydrides, polyurethanes, polyesteramides, polyphosphazenes, polyhydroxybutyrates, polyhdroxyvalerates, polyalkylene oxalates, and copolymers, terpolymers, or combinations or mixtures thereof. Some polymers or copolymers may be either water-soluble or water-insoluble depending upon their molecular weight and ratio of monomers incorporated into the copolymer, e.g. poly(lactide-co-lysine) and poly(lactide-co-malolactonic acid). In order for the drug to be conjugated to these polymers, they must have reactive groups such as hydroxyl, carboxyl, or amine groups. These reactive groups may be either at the terminal ends of the polymers or on side-chains to the main polymer structure. If the reactive groups are terminal groups, the molecular weight of the polymer may need to be relatively low to have enough end groups to achieve the desired drug loading. There are a number of ways to attach a drug to polymers with reactive groups. These include the formation of activated ester groups such as p-nitrophenyl esters, hydroxysuccinimide esters, and the use of dicyclohexyl carbodiimide (DCC). The polymer-drug conjugates may be incorporated into the liquid polymer compositions as either microstructures or macrostructures. They also may be simply dissolved or dispersed in the liquid polymer compositions.

A variety of polymers such as poly(amino acids), poly (amino acid esters), poly(carboxylic acids), poly (hydroxycarboxylic acids), polyorthoesters, polyphosphazenes, polyalkylene glycols and related copolymers have been employed in the preparation of polymer/drug conjugates. For example, poly(amino acids) such as poly-L-aspartic acid, poly(lysine), and poly(glutamic acid) have been utilized in the preparation of polymer/drug conjugates. Related copolymers such as poly(lactic acid-co-lysine) (PLA/Lys) and a poly(ethylene glycol)-poly (aspartic acid) block copolymer have also been employed. Other polymers which are suitable for use in the preparation of polymer/drug conjugates include dextran and copolymers of N-(2-hydroxypropyl)-methacrylamide (HPMA copolymers). The polymers used to prepare drug conjugates may be water-soluble, e.g., polyethylene glycol poly-L-aspartic acid, and poly(lysine), or alternatively may be a water-insoluble polymer such as poly(lactide-co-glycolide) (PLG). Some of the copolymers utilized, e.g., PLA/Lys, may be either water-soluble or water-insoluble depending on the ratio of monomers incorporated into the copolymer. Other examples of thermoplastic polymers which may be employed as the carrier molecule include poly(glycolide), poly(D,L-lactide) (PLA), poly(caprolactone) (PLC) and copolymers of malolactonic acid and D,L-lactide (PLA/MLA).

The liquid delivery composition may consist solely of an organic solvent and a conjugate having the active agent covalently bound to a thermoplastic polymer which is substantially insoluble in aqueous medium, e.g. a low molecular weight PLA or PLG. Alternatively, the composition may include the thermoplastic polymer in unbound form as well as bound to the active agent.

In another embodiment of the present invention, the controlled release component may include a complex in which a carrier molecule is operatively associated with the active agent. The complex may also include a metal cation operatively associated with the active agent and the carrier molecule. For example, the complex may include a biodegradable polymer with carboxyl groups. The carboxyl groups on the polymer may form a coordination complex with a drug and a metal such as zinc, magnesium or calcium. These complexes may break down on contact with water. However, the fact that the drug is part of a complex may prevent the drug from diffusing out of the implant as rapidly as the corresponding free drug.

The controlled release component may include a salt, such as a low water solubility salt of the active agent. For purposes of this invention, the term "low water solubility salt" is defined as a salt which has a solubility of no more than 25 mg/l (25 ppm). The solubility of the low water solubility salt is hereby defined as the amount of salt which can be measured in solution when the salt is dispersed or stirred for 4 hours in distilled water at a temperature of no more than 40° C. The low water solubility salt typically includes a non-toxic, water-insoluble carboxylate anion as a counterion for the active agent (e.g., the anionic form of pamoic acid, tannic acid or stearic acid). This method of reducing the initial burst effect is particularly useful where the active agent is a water soluble bioactive agent such as a peptide (see e.g., U.S. Pat. No. 5,192,741). The low water solubility salt of the active agent may be dispersed in the liquid delivery compositions of the present invention. Alternatively, the low water solubility salt may be microencapsulated or dispersed in the polymeric matrix of a microparticle prior to incorporation into the liquid delivery composition.

The present controlled release components may be prepared from polymers or materials which are either soluble or insoluble in the final liquid delivery composition, i.e., soluble or insoluble in the organic solvent or liquid prepolymer. The polymer or materials used in the preparation is insoluble, the compositions may be prepared and stored as dispersions, e.g., of microparticles or microcapsules. Where the polymer or material is soluble in the bulk liquid composition, the controlled release component may be added and mixed into the composition just prior to its use. The exact time window during which such compositions may be used will depend on the rate of dissolution of the polymer or material in the particular composition. For example, if the polymer or material of the controlled release component is only sparingly soluble in the bulk composition, it may be possible to store the composition as a dispersion or mixture for a limited period of time. Alternatively, if the controlled release component is an active agent conjugate which is soluble in the bulk liquid composition, all of the components of the composition may be blended together to form the liquid composition well in advance of its use.

In one embodiment of the invention, the controlled release component may be dissolved, dispersed or entrained in a solution formulation of a polymer or copolymer to form the liquid delivery composition. The liquid delivery composition typically includes a biodegradable and/or bioerodable, biocompatible polymer or copolymer dissolved in a nontoxic organic solvent. The solvent is miscible or dispersible in aqueous medium, such as body fluids. This liquid composition may be injected or inserted into an implant site of a subject's body. Upon contact with body fluids in the adjacent tissues, the liquid composition solidifies in situ to form a controlled release implant. The controlled release implant is a solid polymer matrix having the controlled release component embedded therewithin.

Alternatively, the controlled release component may be dissolved or dispersed in a liquid formulation of a prepolymer to form the liquid delivery composition. After injection or insertion into an implant site, the prepolymer is cured to form a solid polymeric matrix having the controlled release component embedded there within. The curing step may be carried out with the aid of a curing agent or by other known methods, e.g., by exposing the prepolymer to electromagnetic radiation. If a curing agent is employed, a mixture which includes the prepolymer and the controlled release component is formed. The curing agent is typically added to this mixture to form a liquid prepolymer preparation just prior to injection.

In one embodiment of the present invention, the controlled release component, including the active agent, may be introduced into the body of a subject as part of a liquid composition. The liquid composition includes a biocompatible polymer which is substantially insoluble in aqueous medium, in combination with an organic solvent, and the controlled release component. The organic solvent is miscible or dispersible in aqueous medium. Preferably, the biocompatible polymer is biodegradable and/or bioerodable. The polymer is typically a thermoplastic polymer such as a polylactide, a polycaprolactone or a polyglycolide. The active agent may be a bioactive agent or a diagnostic agent. As used herein, the term "bioactive agent" means a drug, medicament, or some other substance capable of producing an effect on a body. As used herein, the term "diagnostic agent" means a substance, such as an imaging agent, which permits the detection or monitoring of a physiological condition or function. The liquid delivery composition may be injected or inserted into an implant site of the body of the subject. On contact with aqueous medium, such as body fluids in the adjacent tissues, the liquid delivery composition solidifies in situ to form a controlled release implant. The organic solvent of the liquid composition dissipates into surrounding tissue fluids and the polymer coagulates to form a solid implant. The implant is a solid polymer matrix having the controlled release component embedded therewithin. The implant permits the controlled delivery of active agents such as drugs, medicaments, diagnostic agents and the like.

The liquid composition may also be employed to form an implant precursor outside the body. The structure of the implant precursor is composed of an outer sack and a liquid filling. After introduction of the implant precursor into the body of the subject, contact with a body fluid results in the in situ formation of the controlled release implant. The implant precursor includes a mixture of a biocompatible polymer which is substantially insoluble in aqueous medium, the controlled release component which includes the active agent, and an organic solvent which is miscible or dispersible in aqueous medium.

As used herein, the term "implant site" is meant to include a site, in or on which the controlled release implant is to be formed or applied, as for example, a soft tissue such as muscle or fat, or a hard tissue such as bone. Examples of implant sites include a tissue defect such as a tissue regeneration site; a void space such as a periodontal pocket, surgical incision or other formed pocket or cavity; a natural cavity such as the oral, vaginal, rectal or nasal cavities, the cul-de-sac of the eye, and the like; and other sites into which the liquid delivery composition or implant precursor may be placed and formed into a solid implant.

The present liquid delivery composition may include a biocompatible polymer or copolymer in combination with a controlled release component and an organic solvent. As disclosed in U.S. Pat. No. 4,938,763, the disclosure of which is incorporated by reference herein, the organic solvent is biocompatible and miscible or dispersible in aqueous medium. The liquid composition may optionally include a pore-forming agent and/or a physiologically acceptable rate modifying agent. The liquid composition and resulting implant precursor and/or solid implant are biocompatible in that neither the polymer, the solvent, the controlled release component nor the polymer matrix cause substantial tissue irritation or necrosis at the implant site.

The polymers or copolymers are substantially insoluble in aqueous medium, e.g., body fluids, and are biodegradable and bioerodable and/or bioabsorbable within the body of an animal. The term "biodegradable" means that the polymer and/or polymer matrix of the implant will degrade over time by the action of enzymes, by hydrolytic action and/or by other similar mechanisms in the human body. By "bioerodible," it is meant that the implant matrix will erode or degrade over time due, at least in part, to contact with substances found in the surrounding tissue fluids, cellular action, and the like. By "bioabsorbable," it is meant that the polymer matrix will be broken down and absorbed within the human body, for example, by a cell, a tissue, and the like.

Thermoplastic polymers. Thermoplastic polymers useful in the liquid delivery composition include biocompatible polymers that are biodegradable and/or bioerodable and bioabsorbable, and soften when exposed to heat but return to their original state when cooled. The thermoplastic polymers are capable of substantially dissolving in an organic solvent. The thermoplastic polymers are also capable of coagulating or precipitating to form an outer membrane, and an inner core consisting of a solid microporous matrix upon the dissipation of the solvent component from the polymer solution, and the contact of the polymer with an aqueous medium.

Thermoplastic polymers that are suitable for use in the polymer solution generally include any having the foregoing characteristics. Examples are polylactides, polyglycolides, polycaprolactones, polyanhydrides, polyamides, polyurethanes, polyesteramides, polyorthoesters, polydioxanones, polyacetals, polyketals, polycarbonates, polyorthoesters, polyphosphazenes, polyhydroxybutyrates, polyhydroxyvalerates, polyalkylene oxalates, polyalkylene succinates, poly(amino acids), poly(methyl vinyl ether), poly(maleic anhydride), chitin, chitosan, and copolymers, terpolymers, or combinations or mixtures therein. Polylactides, polycaprolactones, polyglycolides and copolymers thereof are highly preferred thermoplastic polymers.

The thermoplastic polymer is combined with a suitable organic solvent to form a solution. The solubility or miscibility of a polymer in a particular solvent will vary according to factors such as crystallinity, hydrophilicity, capacity for hydrogen-bonding, and molecular weight of the polymer. Consequently, the molecular weight and the concentration of the polymer in the solvent are adjusted to achieve desired solubility. Preferably, the thermoplastic polymers have a low degree of crystallization, a low degree of hydrogen-bonding, low solubility in water, and high solubility in organic solvents.

Solvents. Suitable solvents for use in the present liquid delivery composition are those which are biocompatible, pharmaceutically-acceptable, miscible with the polymer ingredient and aqueous medium, and capable of diffusing into an aqueous medium, as for example, tissue fluids surrounding the implant site, such as blood serum, lymph, cerebral spinal fluid (CSF), saliva, and the like. In addition, the solvent is preferably biocompatible. Typically, the solvent has a Hildebrand solubility parameter of from about 9 to about $13(cal/cm^3)^{1/2}$. The degree of polarity of the solvent should be effective to provide at least about 10% solubility in water, and to dissolve the polymer component.

Solvents that are useful in the liquid delivery composition, include, for example, N-methyl-2-pyrrolidone; 2-pyrrolidone; aliphatic alcohols having from two to eight carbon atoms; propylene glycol; glycerol; tetraglycol; glycerol formal; solketal; alkyl esters such as ethyl acetate, ethyl lactate, ethyl butyrate, dibutyl malonate, tributyl citrate, tri-n-hexyl acetylcitrate, diethyl succinate, diethyl glutarate, diethyl malonate, and triethyl citrate; triacetin; tributyrin; diethyl carbonate; propylene carbonate; aliphatic ketones such as acetone and methyl ethyl ketone; dialkylamides such as dimethylacetamide and dimethylformamide; cyclic alkyl amides such as caprolactam; dimethyl sulfoxide; dimethyl sulfone; decylmethylsulfoxide; oleic acid; aromatic amides such as N,N-diethyl-m-toluamide; 1-dodecylazacycloheptan-2-one, and 1,3-dimethyl-3,4,5,6-tetrohydro-2(1H)-pyrimidinone and the like. Preferred solvents according to the present invention include N-methyl-2-pyrrolidone (NMP), 2-pyrrolidone, ethyl lactate, dimethyl sulfoxide (DMSO), and propylene carbonate.

A mixture of solvents providing varying degrees of solubility for the polymer components may be used to increase the coagulation rate of polymers that exhibit a slow coagulation or setting rate. For example, the polymer may be combined with a solvent mixture which includes a good solvent (i.e., a solvent in which the polymer is highly soluble) and a poor solvent (i.e., a solvent in which the polymer has a low degree of solubility) or a non-solvent (i.e., one in which the polymer is insolvent). Preferably, the solvent mixture contains a poor solvent or non-solvent and an effective amount of a good solvent, in admixture such that the polymer will remain soluble while in solution but coagulate or precipitate upon dissipation of the solvents into a surrounding aqueous medium, e.g., tissue fluids at the implant site.

The concentration of polymer in the liquid composition will generally permit rapid and effective dissipation of the solvent and coagulation or precipitation of the polymer. This concentration may range from about 0.01 gram of polymer/ml of solvent to an about saturated concentration, preferably from about 0.1 gram/ml to an about saturated concentration, and more preferably from about 0.2 gram/ml to an about 0.7 gram/ml.

Thermoset Polymers. An in situ forming biodegradable implant can also be constructed by cross-linking appropriately functionalized biodegradable prepolymers. The liquid thermosetting systems of the present invention include the controlled release component and reactive, liquid prepolymers. The liquid prepolymers will cure in situ to form a solid matrix, usually with the aid of a curing catalyst. In general, any biocompatible oligomer which may be linked to a polymerizable functional group to form a biocompatible prepolymer may be utilized. Although any of the biodegradable thermoplastic polymers described herein may be used, the limiting criteria is that low molecular weight oligomers of these polymers must be liquids and must have at least one functional group which can be reacted with a derivatizing agent containing a polymerizable functional group. Suitable liquid prepolymers include oligomers having pendant hydroxyl groups which have been reacted with a derivatizing agent to form a prepolymer having at least one polymerizable ethylenically unsaturated group. For example, a hydroxy terminated low molecular weight polylactide can be reacted with acryloyl chloride to produce an polylactide oligomer end capped with an acrylic ester. The ethylenically unsaturated groups on the prepolymers may then be polymerized by the addition of a curing catalyst, such as a free radical initiator or by exposure to electromagnetic radiation.

Because the prepolymer will remain liquid for a short period of time after addition of a curing agent, a mixture of the liquid prepolymer with a controlled release component and a curing agent may be manipulated, e.g., placed into a syringe and injected into a subject's body. The mixture then forms an solid implant in situ obviating the need for an incision. As with systems based on the thermoplastic polymers, the rate of release of the active agent will be affected by the rates of diffusion of the agent out of the implant. In some instances, the rate of release will be governed by the biodegradation and/or bioerosion of the polymeric matrix implant. In others, the rate of release will be governed by the rate of release of the active agent from the controlled release component.

Active Agent. The liquid delivery compositions of the present invention include an active agent, such as a bioactive agent or a diagnostic agent, either singly or in combination, such that the implant or film dressing will provide a delivery system for the active agent to adjacent or distant tissues and organs in the subject. Bioactive agents which may be used alone or in combination in the implant precursor and implant include, for example, a medicament, drug, or other suitable biologically-, physiologically-, or pharmaceutically-active substance which is capable of providing local or systemic biological, physiological or therapeutic effect in the body of an animal including a mammal, and of being released from the solid implant matrix into adjacent or surrounding tissue fluids. Diagnostic agents which may be used include imaging agents, such as radiodiagnostic agents.

The active agent may be soluble in the polymer solution to form a homogeneous mixture, or insoluble in the polymer solution to form a suspension or dispersion. Upon implantation, the active agent preferably becomes embedded within the implant matrix. As the matrix degrades over time, the active agent is released from the matrix into the adjacent tissue fluids, preferably at a controlled rate. The release of the active agent from the matrix may be varied, for example, by the solubility of the active agent in an aqueous medium, the distribution of the agent within the matrix, the size, shape, porosity, solubility and biodegradability of the implant matrix, and the like.

The liquid delivery composition includes the bioactive agent in an amount effective to provide the desired level of biological, physiological, pharmacological and/or therapeutic effect in the animal. There is generally no critical upper limit on the amount of the bioactive agent included in the liquid delivery composition other than that dictated by the pharmacological properties of the particular bioactive agent. The lower limit of the amount of bioactive agent incorporated into the polymer solution will depend on the activity of the bioactive agent and the period of time desired for treatment.

The bioactive agent may stimulate a biological or physiological activity with the animal. For example, the agent may act to enhance cell growth and tissue regeneration, function in birth control, cause nerve stimulation or bone growth, and the like. Examples of useful bioactive agents include a substance, or metabolic precursor thereof, which is capable of promoting growth and survival of cells and tissues, or augmenting the functioning of cells, as for example, a nerve growth promoting substance such as a ganglioside, a nerve growth factor, and the like; a hard or soft tissue growth promoting agent such as fibronectin (FN), human growth hormone (HGH), protein growth factor interleukin-1 (IL-1), and the like; a bone growth promoting substance such as hydroxyapatite, tricalcium phosphate, and the like; and a substance useful in preventing infection at the implant site, as for example, an antiviral agent such as vidarabine or acyclovir, an antibacterial agent such as a penicillin or tetracycline, an antiparasitic agent such as quinacrine or chloroquine.

Suitable bioactive agents for use in the invention also include anti-inflammatory agents such as hydrocortisone, prednisone and the like; anti-bacterial agents such as penicillin, cephalosporins, bacitracin and the like; antiparasitic agents such as quinacrine, chloroquine and the like; antifungal agents such as nystatin, gentamicin, and the like; antiviral agents such as acyclovir, ribarivin, interferons and the like; antineoplastic agents such as methotrexate, 5-fluorouracil, adriamycin, tumor-specific antibodies conjugated to toxins, tumor necrosis factor, and the like; analgesic agents such as salicylic acid, acetaminophen, ibuprofen, flurbiprofen, morphine and the like; local anaesthetics such as lidocaine, bupivacaine, benzocaine and the like; vaccines such as hepatitis, influenza, measles, rubella, tetanus, polio, rabies and the like; central nervous system agents such as a tranquilizer, B-adrenergic blocking agent, dopamine and the like; growth factors such as colony stimulating factor, platelet-derived growth factor, fibroblast growth factor, transforming growth factor B, human growth hormone, bone morphogenetic protein, insulin-like growth factor and the like; hormones such as progesterone, follicle stimulating hormone, insulin, somatotropins and the like; antihistamines such as diphenhydramine, chlorphencramine and the like; cardiovascular agents such as digitalis, nitroglycerine, papaverine, streptokinase and the like; anti-ulcer agents such as cimetidine hydrochloride, isopropamide iodide, and the like; bronchodilators such as metaproternal sulfate, aminophylline and the like; vasodilators such as theophylline, niacin, minoxidil, and the like; and other like substances. The bioactive agent may also be an antihypertensive agent, an anticoagulant, an antispasmodic agent, or an antipsychotic agent. For additional examples of bioactive agents that may be used in the present invention, see Applicants' corresponding U.S. Pat. No. 5,324,579, issued Jun. 23, 1994, the disclosure of which is incorporated by reference herein.

Accordingly, the formed implant may function as a delivery system of drugs, medicaments, other biologically-active agents and diagnostic agents to tissues adjacent to or distant from the implant site. The active agent is incorporated into the controlled release component. In another embodiment of the invention, the active agent may also be incorporated directly into the polymeric matrix surrounding the controlled release component.

Liquid polymer-drug conjugates. The initial burst of drug from the liquid polymer systems described in U.S. Pat. Nos. 4,938,763, 5,278,201 and 5,278,202 may also be decreased or avoided by conjugating the active agent directly to a water-insoluble biodegradable polymer and dissolving the resultant polymer-drug conjugate in a biocompatible solvent to form a liquid polymer system similar to those described in the above patents. The water-insoluble biocompatible polymers may be those described in these patents or related copolymers. Thus, polyglycolide, poly(D,L-lactide), polycaprolactone, polyorthoesters, polycarbonates, polyamides, polyanhydrides, polyurethanes, polyesteramides, polyphosphazenes, polyhydroxybutryrates, polyhydroxyvalerates, polyalkylene oxalates, and copolymers, terpolymers, or combinations or mixtures thereof with sufficiently low molecular weights to achieve the desired drug loading may be used. Also related copolymers or terpolymers such as poly(lactide-co-malolactonic acid), or combinations or mixtures of the polymers listed above with other polymers may be used to form a solid implant in which the active agent is directly conjugated to the polymer matrix.

The monomer ratios (D,L-lactide versus malolactonic acid) may be varied to obtain the balance of water insolubility and carboxyl group content desired for a particular application. In some instances, in order to obtain a copolymer with the properties desired, it may be advantageous to use other combinations of monomers. For example, MLABE may also be polymerized with glycolide or caprolactone to yield, after removal of the benzyl protecting groups by hydrogenation, poly(glycolide-co-malolactonic acid) or poly(caprolactone-co-malolactonic acid) respectively. Terpolymers such as poly(D,L-lactide/glycolide/malolactonic acid) may also be prepared by the same method.

Pore Structure. The implants formed using the present liquid delivery compositions preferably include a microporous inner core and a microporous outer skin. Typically, the pores of the inner core are substantially uniform and the skin of the solid implant is essentially non-porous compared to the porous nature of the core. Preferably, the outer skin of the implant has pores with diameters significantly smaller in size than these pores in the inner core, e.g., the ratio of the average pore size in the core to the average pore size in the skin is from about 2/1 to about 100/1, and preferably from about 2/1 to about 10/1.

Pores may be formed within the matrix of the implant by several means. The dissipation, dispersement or diffusion of the solvent out of the solidifying polymer matrix into the adjacent tissue fluids may generate pores, including pore channels, in the polymer matrix. The dissipation of the solvent from the coagulating mass creates pores within the solid implant. The size of the pores of the solid implant are in the range of about 1–1000 microns, preferably the size of pores of the skin layer are about 3–500 microns. The solid microporous implant has a porosity in the range of about 5–95%. Preferably the skin has a porosity of 5% to about 10% and the core has a porosity of about 40% to about 60%.

Optionally, a pore-forming agent may be included in the polymer solution to generate additional pores in the polymer matrix. This approach is described more fully in U.S. Pat. No. 5,324,519, issued Jun. 28, 1994, the disclosure of which is incorporated by reference herein. Suitable pore-forming agents include a sugar, a salt, a water-soluble polymer, and a water-insoluble substance that rapidly degrades to a water soluble substance.

Release Rate Modification Agents. The polymer solution may include a release rate modification agent to provide controlled, sustained release of a bioactive agent from the solid implant matrix. Suitable release rate modification agents include an ester of a monocarboxylic acid, an ester of a dicarboxylic acid, an ester of a tricarboxylic acid, a polyhydroxy alcohol, a fatty acid, a triester of glycerol, a sterol, an alcohol, and combinations thereof.

The present invention may be further described by reference to the following examples.

Example 1

Naltrexone/PLA Microparticles in PLG/NMP. A 1:1 melt/fusion mixture was prepared on a Teflon film by melting poly(D,L-lactide) (PLA; approx. 2,000 MW; Boehringer-Ingleheim; Resomer L104) and adding an equal quantity of naltrexone base. The melt was then allowed to cool to a fused solid. The fused solid was separated from the Teflon film and ground to a fine powder. A five percent w/w formulation of naltrexone was prepared by adding 30 mg of the melt/fused naltrexone/PLA powder to 300 mg of a solution of poly(D,L-lactide-co-glycolide) (PLG) in N-methylpyrrolidone (NMP). A 5% w/w control formulation of naltrexone was prepared by adding 15 mg of unprocessed naltrexone base to 300 mg of the PLG/NMP solution. The in-vitro release of naltrexone from each of the formulations was evaluated by adding a drop of formulation to a five ml aliquot of phosphate buffered saline solution (PBS) in a 10 ml vial. The amount of naltrexone released was determined by storing the vial at 37° C. and monitoring the absorbance at 280 nm as a function of time. The results (shown in FIG. 1) indicate that the formulation which included the microparticles of melt/fused naltrexone/PLA dispersed in the PLG/NMP solution significantly reduced the initial release of naltrexone (in comparison with the control solution of naltrexone in PLG/NMP).

Example 2

Ganirelix Microparticles in PLG/NMP. Ganirelix acetate (a GnRH antagonist suitable for treating endometriosis and prostate carcinoma) was incorporated in microparticles of a solvent-insoluble, fast-biodegrading polymer. This was done to decrease the solubility of ganirelix in the polymer/solvent formulation and to enhance the dispersing characteristics of the ganirelix acetate in this same formulation. Ganirelix acetate (6 gm) and poly(sebacic acid) (4 gm; "PSA") were mixed to form a homogenous powder mixture. The powder mixture was melted on a hotplate at 80° C. and mixed until the ganirelix acetate was homogeneously dispersed in the PSA melt. The ganirelix acetate/PSA melt was allowed to cool to room temperature to form a solid, which was then ground in a Cryo-Mill for one minute to form a fine powder. The powder was sieved to collect the particles of less than 60 microns. A 50:50 solution of PLA in ethyl lactate was formed by dissolving an equal amount of PLA in ethyl lactate using a sonicator at 45° C. The final formulation was prepared by adding 1.14 gm of the ganirelix acetate/PSA microparticles to 4 ml of the PLA/ethyl lactate solution. The resulting mixture, which was mixed well by shaking, could be administered through a 20 gauge needle. Due to the solubility of PSA in ethyl lactate, this formulation was used within one hour of mixing. A relatively large burst effect is observed with formulations where ganirelix is simply dissolved in the PLA/NMP solution (>10% during the first day after administration). This initial burst of ganirelix can cause local tissue irritation and is clinically unacceptable. In vitro and in vivo experiments demonstrated that the liquid composition with the ganirelix acetate/PSA microparticles eliminated the high initial release of ganirelix (<3% during the first day after administration).

Example 3

Porcine Somatotrophin Microcapsules in PLA/NMP. A PLA/NMP stock solution is prepared by dissolving PLA (2000 MW) in an equal amount of N-methylpyrrolidone (50:50 PLA/NMP). A liquid composition containing porcine somatotropin (PST) microcapsules is prepared by adding 0.2 g of microcapsules containing 41% by weight PST in a carboxymethyl cellulose matrix to 2.0 g of the PLA/NMP solution. A similar formulation is prepared by adding microcapsules containing PST in a gelatin matrix to the 50:50 PLA/NMP solution. The in vitro release of PST from these formulations is examined by dispensing the formulation (150–300 microliters) through a 20 gauge needle directly into 10 ml of phosphate buffered saline. The rate of release from the microcapsule formulations is significantly lower than the initial release of PST from the microcapsules alone.

Example 4

Figure 2:
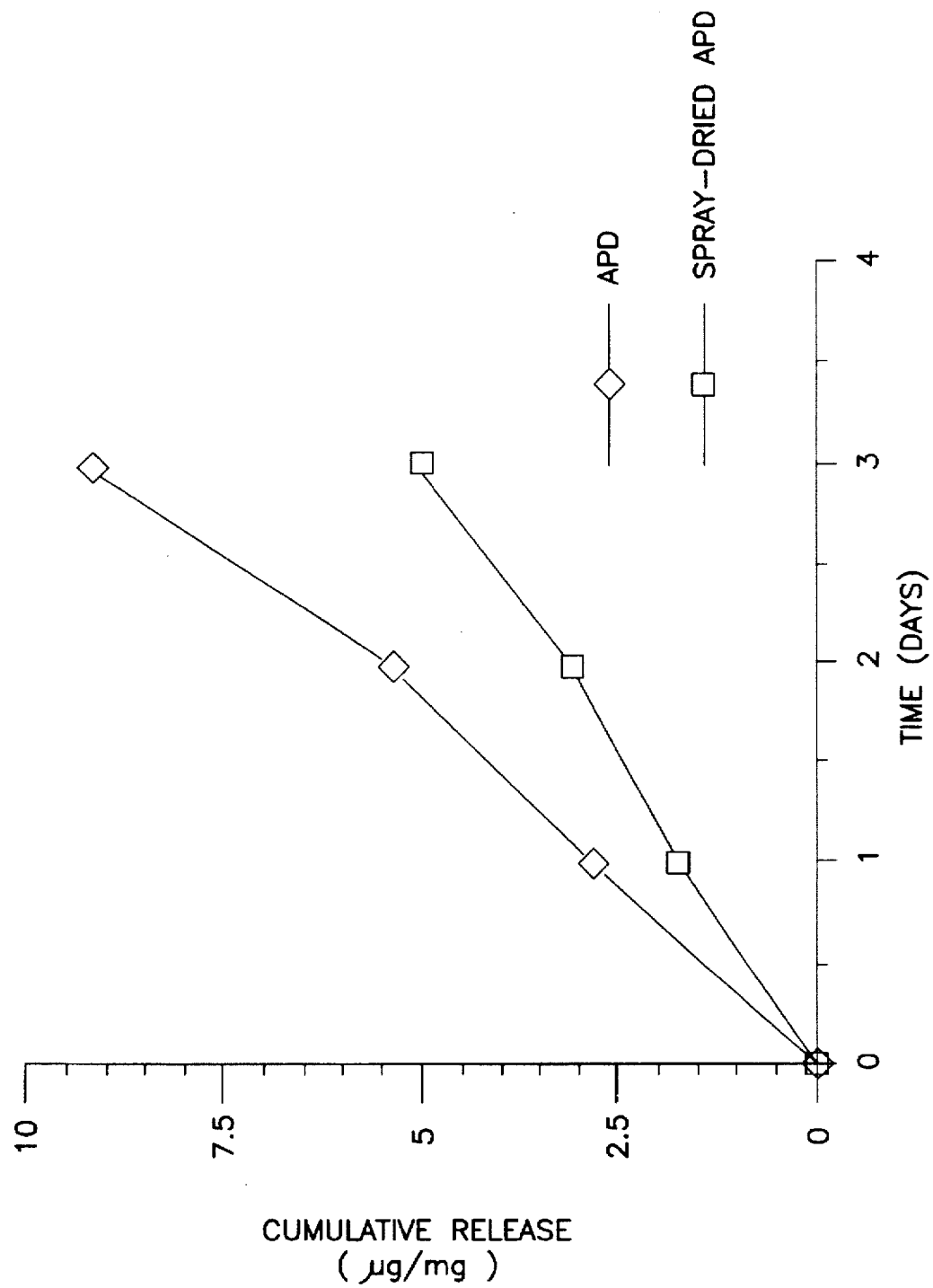
FIG. 2 shows the cumulative amount of an antipsychotic drug (APD) released from formulations in 75/25 PLG dissolved in NMP. The formulations included either free APD or APD encapsulated with high molecular weight poly(vinyl pyrrolidinone) ("PVP"). Each of the formulations contained 5.0% w/w APD (on a free drug basis).

Microencapsulated Antipsychotic Drug in PLG/NMP. Seventeen (17.0) grams of a benzisoazolpyrimidinone antipsychotic drug (APD) may be added to an aqueous solution (17.0 g polymer in 300 ml water) of a water-soluble, biodegradable polymer, poly(vinyl pyrrolidinone) ("PVP"; MW 100,000). The resulting preparation is a well dispersed suspension. This suspension is spray dried using a Büuchi 190 mini spray drier with the following parameters: heating rate of 11, aspiration rate of 20, compressed air pressure of 80 psi, air flow of 800 NL/hr, nozzle opening of 0.7 mm, inlet temperature of 167° C., and an outlet temperature of 103° C. After 75 min. of processing using the above conditions, 3.2 g of fine powder of APD encapsulated in PVP is obtained. A 5% w/w formulation of APD in dispersed in polymer solution may be prepared by adding 27 mg of the PVP-encapsulated particles to a solution of poly(D,L-lactide-co-glycolide) (60% 75/25 PLG (0.11)) in NMP. A control formulation was prepared by adding untreated APD (13.5 mg) to the same 60% PLG/NMP solution. The in-vitro release of APD from these formulations may be evaluated by adding a drop of the respective formulations to 5.0 ml aliquots of buffer solution (in 10 ml vials) and storing at 37° C. The absorbance is monitored at 280 nm as a function of time. The results indicate that coating the solid APD particles with a high molecular weight water soluble polymer reduces the initial release of APD (see FIG. 2).

Example 5

Figure 3:
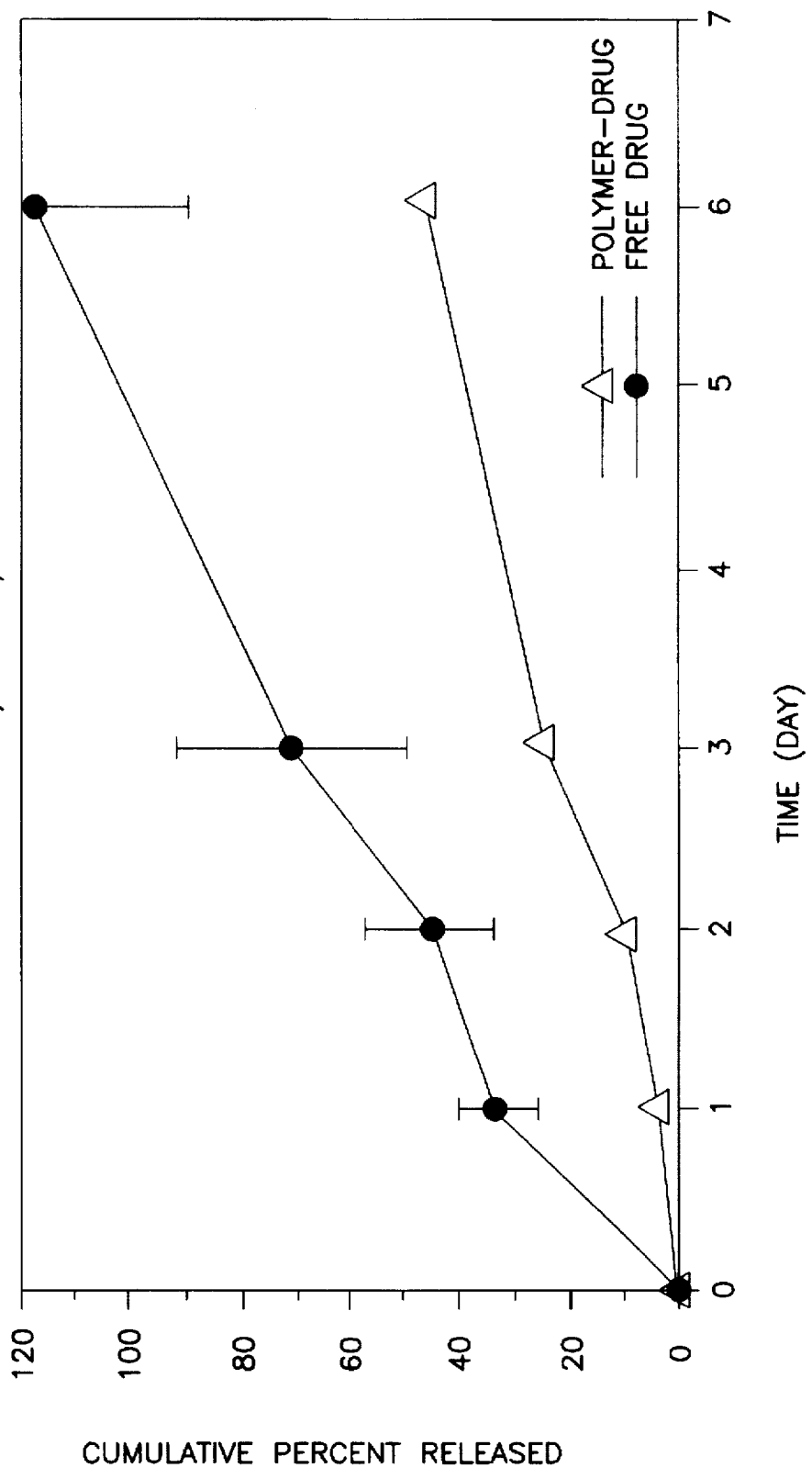
FIG. 3 shows the cumulative amount of chlorin $e_6$ released from formulations in 75/25 PLG dissolved in DMSO. The formulations included either free chlorin $e_6$ and chlorin $e_6$ covalently bound to an (N-2-hydroxypropyl)

Polymer-Bound Chlorin $e_6$ in PLG/DMSO. A conjugate of chlorin $e_6$ covalently bound to an N-(2-hydroxypropyl) methacrylamide/N-methacryloylglycine copolymer (HPMA copolymer) containing glycyl side chains was prepared according to the procedures described in Krinick, Ph.D. Dissertation: Combination Polymeric Drugs as Anticancer Agents, University of Utah (1992). The conjugate contained 11 wt. % chlorin $e_6$ and 89 wt. % HMPA copolymer. The chlorin $e_6$ was bound to the HPMA copolymer through the carboxyl groups of the pendant glycine residues. Two formulations were prepared, each containing 0.5 wt. % chlorin $e_6$ (on a free drug basis). One of the formulations contained 53 wt. % PLG (iv=0.11 dl/g), 46.5 wt. % DMSO and 0.5 wt. % free chlorin $e_6$. The second formulation 51 wt. % PLG, 44.75 wt. % DMSO and 4.25 wt. % of the chlorin $e_6$/HMPA copolymer conjugate. Drops of the two formulations were precipitated into 5 ml of phosphate buffered saline and the samples were placed on an environmental shaker at 37° C. The concentration of chlorin $e_6$ in the solution was monitored as a function of time using UV/visible spectroscopy ($\lambda_{max}$=650 nm). The cumulative percentage of drug released is shown in FIG. 3. The results indicated that chlorin $e_6$ is released much more slowly from the formulation which contains the chlorin $e_6$/HMPA copolymer conjugate. In addition, no burst effect was observed from the chlorin $e_6$/HMPA copolymer conjugate formulation.

Example 6

PLA/MLA-p-doxorubicin in PLG/NMP. A water-soluble copolymer of D,L-lactide with malolactonic acid (PLA/MLA) may be prepared by initially copolymerizing D,L-lactide with malolactonic acid monobenzyl ester (MLABE). The benzyl protecting groups may be removed from the resultant copolymer by hydrogenation to yield a copolymer (PLA/MLA) with free carboxyl side chain groups. The free carboxyl groups may be reacted with dicyclohexylcarbodiimide and p-nitrophenol to yield a PLA/MLA copolymer with pendant p-nitrophenol ester groups. Doxorubicin may be attached to the PLA/MLA copolymer via an aminolysis reaction to yield a PLA/MLA-p-doxorubicin copolymer.

Sufficient PLA/MLA-p-doxorubicin may be added to a 60:40 PLG/NMP stock solution to form a liquid composition having 2.0% by weight doxorubicin (on a free doxorubicin basis). A control formulation of free doxorubicin may be prepared by adding 20 mg of doxorubicin to 980 mg of the 60:40 PLG/NMP stock solution. The in vitro release of doxorubicin from each of the formulations may be evaluated by adding a drop of formulation to a five ml aliquot of phosphate buffered saline solution (PBS) in a 10 ml vial. The free doxorubicin formulation may show a substantial initial burst of the drug. Essentially no doxorubicin may be released over a period of 3 days from a sample which includes the PLA/MLA-p-doxorubicin. The in vitro determination may be repeated by adding a drop of formulation to a five ml aliquot of rabbit peritoneal fluid in a 10 ml vial. The free doxorubicin formulation may show a substantial initial burst of doxorubicin. The PLA/MLA-p-doxorubicin containing composition may show no burst and the rate of doxorubicin release may be much lower than the rate observed for the free doxorubicin formulation.

Example 7

PLG-t-Doxorubicin in PLG/NMP. Low molecular weight poly(D,L-lactide-co-glycolide) (PLG) with terminal carboxyl groups may be reacted with dicyclohexylcarbodiimide and p-nitrophenol to yield a PLG copolymer with terminal p-nitrophenol ester groups. Doxorubicin may then be reacted with the p-nitrophenol ester groups to give a PLG copolymer with doxorubicin attached to the terminal carboxyl groups of the copolymer (PLG-t-doxorubicin).

The PLG-t-doxorubicin conjugate may then be added to 60:40 PLG/NMP stock solution to form a liquid composition having 2.0% by weight doxorubicin (on a free dosxorubicin basis). The rate of release of doxorubicin in PBS and rabbit peritoneal fluid may be determined using standard methods. As is observed with the PLA/MA-p-doxorubicin composition, essentially no doxorubicin may be released over a period of 3 days from the addition of the sample which includes the PLG-t-doxorubicin to PBS. No burst effect may be effect may be observed with the addition of a drop of the PLG-t-doxorubicin composition to rabbit peritoneal fluid. Once again, the rate of doxorubicin release into rabbit peritoneal fluid from the PLG-t-doxorubicin composition may be much lower than the rate observed for the free doxorubicin formulation.

All publications and patent applications in this specification are indicative of the level of ordinary skill in the art to which this invention pertains. All publications and patent applications cited herein are incorporated by reference to the same extent as if each individual publication or patent application was specifically and individually incorporated by reference.

The invention has been described with reference to various specific and preferred embodiments and techniques. However, it should be understood that many variations and modifications may be made while remaining within the spirit and scope of the invention.

What is claimed is:

1. A method for the in situ formation of a controlled release implant in or on a subject, comprising:

administering to the subject a flowable composition, and allowing the flowable composition to contact a body fluid of the subject or an aqueous medium to form the controlled release said implant within or on the subject; wherein, the flowable composition comprises an organic solvent in which is dissolved a thermoplastic polymer, and in which is suspended a multiplicity of solid microstructures incorporating an active agent;

the organic solvent is biocompatible, and has a solubility range of miscible to dispersible in the aqueous medium or the body fluid;

the thermoplastic polymer is biocompatible, biodegradable, soluble in the organic solvent, and insoluble in the aqueous medium or the body fluid;

the solid microstructures are insoluble in the organic solvent, the aqueous medium and the body fluid, and are composed of a biocompatible polymer which is biodegradable.

2. A method of treating a subject with an active agent, comprising:

inserting into the subject a controlled release implant which is formed outside the subject by contacting a flowable composition with an aqueous medium; wherein, the flowable composition comprises an organic solvent in which is dissolved a thermoplastic polymer and in which is suspended a multiplicity of solid microstructures incorporating an active agent;

the organic solvent is biocompatible, and has a solubility range of miscible to dispersible in the aqueous medium;

the thermoplastic polymer is biocompatible, biodegradable, soluble in the organic solvent, and insoluble in the aqueous medium and a body fluid of the subject;

the solid microstructures are insoluble in the organic solvent, the aqueous medium and the body fluid, and are composed of a biocompatible polymer which is biodegradable.

3. The method of claim 1 wherein administering the composition comprises spraying, painting or squirting the composition on the tissue.

4. The method of claim 1, wherein the biocompatible, thermoplastic polymer is selected from the group consisting of polylactides, polyglycolides, polycaprolactones, polyanhydrides, polyamides, polyurethanes, polyesteramides, polydioxanones, polyacetals, polyketals, polycarbonates, polyorthoesters, polyphosphazenes, polyhydroxybutyrates, polyhydroxyvalerates, polyalkylene oxalates, polyalkylene succinates, poly(amino acids), copolymers thereof, terpolymers thereof, and mixtures thereof.

5. The method of claim 1, wherein the thermoplastic polymer is selected from the group consisting of polylactides, polycaprolactones, and polyglycolides.

6. The method of claim 1, wherein the organic solvent is selected from the group consisting of N-methyl-2-pyrrolidone, 2-pyrrolidone, glycerol, tetraglycol, glycerol formal, solketal, ethyl acetate, ethyl lactate, ethyl butyrate, dibutyl malonate, tributyl citrate, tri-n-hexyl acetylcitrate, diethyl succinate, diethyl glutarate, diethyl malonate, triethyl citrate, triacetin, tributyrin, diethyl carbonate, propylene carbonate, acetone, methyl ethyl ketone, dimethyl sulfoxide, dimethyl sulfone, tetrahydrofuran, caprolactam, N,N-diethyl-m-toluamide, 1-dodecylazacycloheptan-2-one, 1,3-dimethyl-3,4,5,6-tetrohydro-2(1H)-pyrimidinone, and any combination thereof.

7. The method of claim 1, wherein the organic solvent is selected from the group consisting of N-methyl-2-pyrrolidone, 2-pyrrolidone, ethyl lactate, dimethyl sulfoxide, propylene carbonate, and any combination thereof.

8. The method of claim 1, wherein the active agent is selected from the group consisting of an antibacterial agent, antifungal agent, antiviral agent, anti-inflammatory agent, antiparasitic agent, anti-neoplastic agent, analgesic agent, anesthetic agent, antipsychotic agent, vaccine, central nervous system agent, growth factor, hormone, antihistamine, osteoinductive agent, cardiovascular agent, anti-ulcer agent, bronchodilating agent, vasodilating agent, birth control agent, antihypertensive agent, anticoagulant, antispasmodic agent, fertility-enhancing agent, and combinations thereof.

9. A method according to claim 7 or 8, wherein the microstructures are microparticles, microcapsules or nanoparticles.

* * * * *